US010588762B2

(12) United States Patent
Gill et al.

(10) Patent No.: US 10,588,762 B2
(45) Date of Patent: Mar. 17, 2020

(54) ESOPHAGEAL STENT

(71) Applicant: Merit Medical Systems, Inc., South Jordan, UT (US)

(72) Inventors: Darla Gill, Salt Lake City, UT (US); Zeke Eller, Plano, TX (US); Rich Snider, Dallas, TX (US); Trent Clegg, College Place, WA (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/202,128

(22) Filed: Mar. 10, 2014

(65) Prior Publication Data

US 2014/0277573 A1 Sep. 18, 2014

Related U.S. Application Data

(60) Provisional application No. 61/787,756, filed on Mar. 15, 2013.

(51) Int. Cl.
*A61F 2/90* (2013.01)
*A61F 2/24* (2006.01)
(Continued)

(52) U.S. Cl.
CPC .............. *A61F 2/90* (2013.01); *A61F 2/24* (2013.01); *A61F 2/07* (2013.01);
(Continued)

(58) Field of Classification Search
CPC .............. A61F 2/04; A61F 2002/044; A61F 2002/046; A61F 2/06; A61F 2/24;
(Continued)

(56) References Cited

U.S. PATENT DOCUMENTS 5,061,275 A 10/1991 Wallsten et al.
5,152,797 A 10/1992 Luckman et al.
(Continued)

FOREIGN PATENT DOCUMENTS

CN 1433818 A 8/2003
CN 201200504 3/2009
(Continued)

OTHER PUBLICATIONS

International Search Report and Written Opinion dated Mar. 29, 2013 for PCT/US2012/060364.
(Continued)

*Primary Examiner* — Suba Ganesan
*Assistant Examiner* — Aren Patel
(74) *Attorney, Agent, or Firm* — Stoel Rives LLP

(57) ABSTRACT

Implantable device embodiments, such as stents, and particularly esophageal stents, formed of a scaffolding structure are disclosed. The scaffolding structure is formed of one or more strand elements arranged in a braided pattern. A covering may coat the scaffolding structure. A valve can be secured to the scaffolding structure and/or the covering. Anti-migration features may be formed by bends in the one or more strand elements. The bends forming the anti-migration features protrude outwardly away from an outer surface of the implantable device.

23 Claims, 11 Drawing Sheets

(51) Int. Cl.
*A61F 2/04* (2013.01)
*A61F 2/07* (2013.01)

(52) U.S. Cl.
CPC . *A61F 2002/044* (2013.01); *A61F 2230/0013* (2013.01); *A61F 2250/0018* (2013.01); *A61F 2250/0039* (2013.01)

(58) Field of Classification Search
CPC ...... A61F 2/82; A61F 2/90; A61F 2250/0018; A61F 2250/0039; A61F 2230/0013; A61F 2/07
See application file for complete search history.

(56) References Cited

U.S. PATENT DOCUMENTS

| | | | |
|---|---|---|---|
| 5,314,473 A | | 5/1994 | Godin |
| 5,607,445 A * | | 3/1997 | Summers ................. 623/1.22 |
| 5,662,713 A | | 9/1997 | Andersen et al. |
| 5,733,327 A * | | 3/1998 | Igaki .................... A61F 2/86 623/1.5 |
| 5,766,263 A | | 6/1998 | Grundei et al. |
| 5,827,321 A | | 10/1998 | Roubin et al. |
| 5,833,707 A | | 11/1998 | McIntyre et al. |
| 5,843,175 A | | 12/1998 | Frantzen |
| 6,221,091 B1 | | 4/2001 | Khosravi |
| 6,254,642 B1 | | 7/2001 | Taylor |
| 6,264,700 B1 | | 7/2001 | Kilcoyne et al. |
| 6,302,917 B1 | | 10/2001 | Dua et al. |
| 6,348,065 B1 | | 2/2002 | Brown et al. |
| 6,464,720 B2 | | 10/2002 | Boatman et al. |
| 6,511,505 B2 | | 1/2003 | Cox et al. |
| 6,544,291 B2 | | 4/2003 | Taylor |
| 6,585,758 B1 * | | 7/2003 | Chouinard ............... A61F 2/90 623/1.16 |
| 6,635,082 B1 * | | 10/2003 | Hossainy et al. ............ 623/1.15 |
| 6,669,724 B2 | | 12/2003 | Park et al. |
| 6,701,174 B1 | | 3/2004 | Krause et al. |
| 6,845,776 B2 | | 1/2005 | Stack et al. |
| 6,878,162 B2 | | 4/2005 | Bales et al. |
| 6,913,619 B2 | | 7/2005 | Brown et al. |
| 6,929,658 B1 | | 8/2005 | Freidberg et al. |
| 6,966,928 B2 | | 11/2005 | Fell et al. |
| 6,991,647 B2 | | 1/2006 | Jadhav |
| 7,182,788 B2 | | 2/2007 | Jung |
| 7,462,192 B2 | | 12/2008 | Norton et al. |
| 7,488,347 B1 | | 2/2009 | Goble et al. |
| 7,547,321 B2 | | 6/2009 | Silvestri et al. |
| 7,637,942 B2 | | 12/2009 | Mangiardi et al. |
| 7,641,694 B1 | | 1/2010 | Goble et al. |
| 7,695,446 B2 | | 4/2010 | Levine et al. |
| 7,722,624 B2 | | 5/2010 | Boucher et al. |
| 8,114,045 B2 | | 2/2012 | Surti |
| 8,361,147 B2 | | 1/2013 | Shterling et al. |
| 8,500,821 B2 | | 8/2013 | Sobrino-Serrano et al. |
| 8,523,936 B2 | | 9/2013 | Schmid et al. |
| 8,579,985 B2 | | 11/2013 | Podolsky et al. |
| 8,632,600 B2 | | 1/2014 | Zannis et al. |
| 8,986,368 B2 | | 3/2015 | Gill et al. |
| 2002/0032479 A1 | | 3/2002 | Hankh et al. |
| 2002/0068967 A1 * | | 6/2002 | Drasler et al. ............. 623/1.13 |
| 2002/0107565 A1 | | 8/2002 | Greenhalgh |
| 2002/0116052 A1 | | 8/2002 | Cox et al. |
| 2002/0138135 A1 | | 9/2002 | Duerig et al. |
| 2003/0009236 A1 | | 1/2003 | Godin |
| 2003/0060884 A1 | | 3/2003 | Fell et al. |
| 2003/0109878 A1 | | 6/2003 | Grundei |
| 2003/0109879 A1 | | 6/2003 | Grundei |
| 2003/0135265 A1 * | | 7/2003 | Stinson .................... A61F 2/90 623/1.16 |
| 2003/0220700 A1 | | 11/2003 | Hammer et al. |
| 2004/0019374 A1 | | 1/2004 | Hojeibane et al. |
| 2004/0044396 A1 * | | 3/2004 | Clerc .................... A61F 2/07 623/1.13 |
| 2004/0044401 A1 | | 3/2004 | Bales et al. |
| 2004/0068324 A1 | | 4/2004 | Grundei |
| 2004/0088040 A1 | | 5/2004 | Mangiardi et al. |
| 2004/0098099 A1 * | | 5/2004 | McCullagh ............... A61F 2/90 623/1.15 |
| 2004/0102866 A1 | | 5/2004 | Harris et al. |
| 2004/0107004 A1 | | 6/2004 | Levine et al. |
| 2004/0116996 A1 | | 6/2004 | Freitag |
| 2004/0127973 A1 | | 7/2004 | Mangiardi et al. |
| 2004/0204749 A1 | | 10/2004 | Gunderson |
| 2004/0236424 A1 | | 11/2004 | Berez et al. |
| 2004/0267350 A1 | | 12/2004 | Roubin et al. |
| 2005/0033424 A1 | | 2/2005 | Fell |
| 2005/0080491 A1 | | 4/2005 | Levine et al. |
| 2005/0102038 A1 | | 5/2005 | Grundei |
| 2005/0143745 A1 | | 6/2005 | Hadorek et al. |
| 2005/0169893 A1 | | 8/2005 | Koblish et al. |
| 2005/0183731 A1 | | 8/2005 | Hunter et al. |
| 2006/0157543 A1 | | 7/2006 | Abkowitz et al. |
| 2006/0212052 A1 | | 9/2006 | Shin et al. |
| 2006/0253190 A1 | | 11/2006 | Kuo |
| 2006/0259137 A1 | | 11/2006 | Artof et al. |
| 2006/0276874 A1 | | 12/2006 | Wilson et al. |
| 2007/0038290 A1 * | | 2/2007 | Huang .................... A61F 2/90 623/1.16 |
| 2007/0050011 A1 | | 3/2007 | Klein et al. |
| 2007/0050021 A1 | | 3/2007 | Johnson |
| 2007/0100437 A1 | | 5/2007 | Welborn et al. |
| 2007/0112437 A1 | | 5/2007 | Shank |
| 2007/0150049 A1 | | 6/2007 | Nissl |
| 2007/0173946 A1 | | 7/2007 | Bonutti |
| 2007/0198022 A1 | | 8/2007 | Lang et al. |
| 2007/0198097 A1 | | 8/2007 | Zegid |
| 2007/0239273 A1 | | 10/2007 | Allen |
| 2007/0255412 A1 | | 11/2007 | Hajaj et al. |
| 2007/0276463 A1 | | 11/2007 | Nissl et al. |
| 2008/0004688 A1 | | 1/2008 | Spenser et al. |
| 2008/0097579 A1 | | 4/2008 | Shanley et al. |
| 2008/0132998 A1 | | 6/2008 | Mangiardi et al. |
| 2008/0133020 A1 | | 6/2008 | Blackwell et al. |
| 2008/0140181 A1 | | 6/2008 | Reynolds et al. |
| 2008/0154351 A1 | | 6/2008 | Leewood et al. |
| 2008/0200979 A1 | | 8/2008 | Dieck et al. |
| 2008/0221664 A1 | | 9/2008 | Bales et al. |
| 2008/0221670 A1 * | | 9/2008 | Clerc .................... A61F 2/07 623/1.34 |
| 2008/0243225 A1 | | 10/2008 | Satasiya et al. |
| 2008/0288044 A1 | | 11/2008 | Osborne |
| 2009/0036976 A1 | | 2/2009 | Beach et al. |
| 2009/0043373 A1 * | | 2/2009 | Arnault De La Menardiere et al. ............... 623/1.15 |
| 2009/0105809 A1 | | 4/2009 | Lee et al. |
| 2009/0118830 A1 | | 5/2009 | Fell |
| 2009/0171456 A1 | | 7/2009 | Kveen et al. |
| 2009/0171465 A1 | | 7/2009 | Bucay-Couto et al. |
| 2009/0187240 A1 * | | 7/2009 | Clerc .................... A61F 2/07 623/1.17 |
| 2009/0240320 A1 | | 9/2009 | Tuval et al. |
| 2010/0004728 A1 | | 1/2010 | Rao et al. |
| 2010/0036504 A1 | | 2/2010 | Sobrino-Serrano et al. |
| 2010/0082093 A1 * | | 4/2010 | Weber ..................... 623/1.15 |
| 2010/0114327 A1 | | 5/2010 | Sobrino-Serrano |
| 2010/0121461 A1 * | | 5/2010 | Sobrino-Serrano et al. ............... 623/23.68 |
| 2010/0121462 A1 | | 5/2010 | Sobrino-Serrano et al. |
| 2010/0137998 A1 | | 6/2010 | Sobrino-Serrano et al. |
| 2010/0173066 A1 | | 7/2010 | Mangiardi et al. |
| 2010/0256744 A1 | | 10/2010 | Laborde et al. |
| 2010/0286760 A1 | | 11/2010 | Beach et al. |
| 2011/0004290 A1 | | 1/2011 | Bales, Jr. et al. |
| 2011/0054592 A1 | | 3/2011 | Fliedner |
| 2011/0160836 A1 | | 6/2011 | Behan |
| 2011/0190874 A1 | | 8/2011 | Celermajer et al. |
| 2011/0190905 A1 | | 8/2011 | Behan |
| 2011/0265908 A1 * | | 11/2011 | Clerc .................... A61F 2/90 140/71 R |
| 2011/0319980 A1 | | 12/2011 | Ryan |
| 2012/0010697 A1 | | 1/2012 | Shin et al. |
| 2012/0059486 A1 | | 3/2012 | Sobrino-Serrano et al. |

(56) References Cited

U.S. PATENT DOCUMENTS

| | | |
|---|---|---|
| 2012/0071987 A1 | 3/2012 | Levy |
| 2013/0006382 A1 | 1/2013 | Behan |
| 2013/0103163 A1* | 4/2013 | Krimsky ............... A61F 2/04 623/23.65 |

FOREIGN PATENT DOCUMENTS

| | | | |
|---|---|---|---|
| CN | 201500504 | 6/2010 | |
| DE | 102010046459 | 3/2012 | |
| EP | 0880948 | 12/1998 | |
| EP | 1870057 | 12/2007 | |
| EP | 2085050 A1 | 5/2009 | |
| EP | 2005050 | 8/2009 | |
| EP | 2085050 A1 * | 8/2009 | ............... A61F 2/04 |
| EP | 2329796 | 6/2011 | |
| EP | 2489331 | 8/2012 | |
| WO | 2005089672 | 9/2005 | |
| WO | WO2005/089672 | 9/2005 | |
| WO | 2006047520 A2 | 5/2006 | |
| WO | WO2006/047520 | 5/2006 | |
| WO | 2006069094 A1 | 6/2006 | |
| WO | WO2006/069094 | 6/2006 | |
| WO | 2009153768 | 12/2009 | |
| WO | 2010098857 | 9/2010 | |
| WO | WO2010/098857 | 9/2010 | |
| WO | 2011104269 | 9/2011 | |
| WO | WO2011/104269 | 9/2011 | |
| WO | WO2012/103501 | 8/2012 | |

OTHER PUBLICATIONS

Office Action dated May 15, 2013 for U.S. Appl. No. 13/285,358.
Material Safety Data Sheet, © 2010 Polymer Systems Technology Limited™, UK & Ireland Distributor, NUSIL Silicone Technology. Effective Feb. 8, 2010, pp. 1-9.
International Search Report and Written Opinion dated Aug. 16, 2012 for PCT/US2012/035851.
Office Action dated Nov. 6, 2012 for U.S. Appl. No. 13/153,150.
Office Action dated Apr. 18, 2013 for U.S. Appl. No. 13/153,150.
International Search Report and Written Opinion dated Sep. 13, 2013 for PCT/US2013/044013.
Office Action dated Jan. 6, 2014 for U.S. Appl. No. 13/285,358.
Office Action dated Jun. 19, 2014 for U.S. Appl. No. 13/153,150.
Restriction Requirement dated May 6, 2014 for U.S. Appl. No. 13/909,427.
Office Action dated Jan. 13, 2015 for U.S. Appl. No. 13/153,150.
Office Action dated Jan. 29, 2015 for U.S. Appl. No. 13/352,926.
European Search Report dated Feb. 18, 2015 for EP12793791.0.
Office Action dated Mar. 13, 2015 for U.S. Appl. No. 14/196,012.
Office Action dated Oct. 17, 2014 for U.S. Appl. No. 13/909,427.
Office Action dated Jun. 30, 2015 for U.S. Appl. No. 13/909,427.
International Search Report and Written Opinion dated May 15, 2014 for PCT/US2012/060364.
International Search Report and Written Opinion dated Jun. 10, 2014 for PCT/US2014/020187.
International Search Report and Written Opinion dated Jul. 1, 2014 for PCT/US2014/022328.
International Search Report and Written Opinion datedOct. 16, 2012 for PCT/US2012/060364.
Notice of Allowance dated Dec. 23, 2014 for U.S. Appl. No. 13/285,358.
Office Action dated Sep. 10, 2015 for U.S. Appl. No. 13/153,150.
Office Action dated Feb. 17, 2016 for U.S. Appl. No. 14/196,012.
Office Action dated Jun. 19, 2014 for U.S. Appl. No. 13/352,926.
Office Action dated Sep. 28, 2015 for U.S. Appl. No. 14/196,012.
Extended European Search Report dated Sep. 9, 2016 for EP14767746.2.
Notice of Allowance dated Aug. 26, 2016 for U.S. Appl. No. 14/196,012.
Office Action dated Mar. 22, 2016 for U.S. Appl. No. 14/661,562.
Office Action dated Apr. 27, 2016 for U.S. Appl. No. 13/153,150.
Office Action dated May 11, 2016 for U.S. Appl. No. 13/909,427.
Office Action dated Oct. 25, 2016 for U.S. Appl. No. 14/661,562.
Office Action dated Dec. 19, 2016 for U.S. Appl. No. 13/909,427.
Notice of Allowance dated May 18, 2017 for U.S. Appl. No. 14/661,562.
Office Action dated Feb. 8, 2017 for U.S. Appl. No. 13/153,150.
Notice of Allowance dated May 5, 2017 for U.S. Appl. No. 13/909,427.
Office Action dated Feb. 23, 2018 for U.S. Appl. No. 13/153,150.
Office Action dated Aug. 24, 2017 for U.S. Appl. No. 13/153,150.
Notice of Allowance dated Mar. 6, 2019 for U.S. Appl. No. 13/153,150.
Office Action dated Oct. 16, 2018 for U.S. Appl. No. 13/153,150.

* cited by examiner

ESOPHAGEAL STENT

RELATED APPLICATIONS

This application claims priority to U.S. Provisional Patent Application No. 61/787,756, titled ESOPHAGEAL STENT, filed on Mar. 15, 2013, which is hereby incorporated herein by reference in its entirety.

TECHNICAL FIELD

The present disclosure relates generally to devices configured to be implanted within a body lumen. More particularly, the present disclosure relates to stents or similar prosthetic devices which, in certain embodiments, are configured to be disposed within the esophagus and which may comprise a valve.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
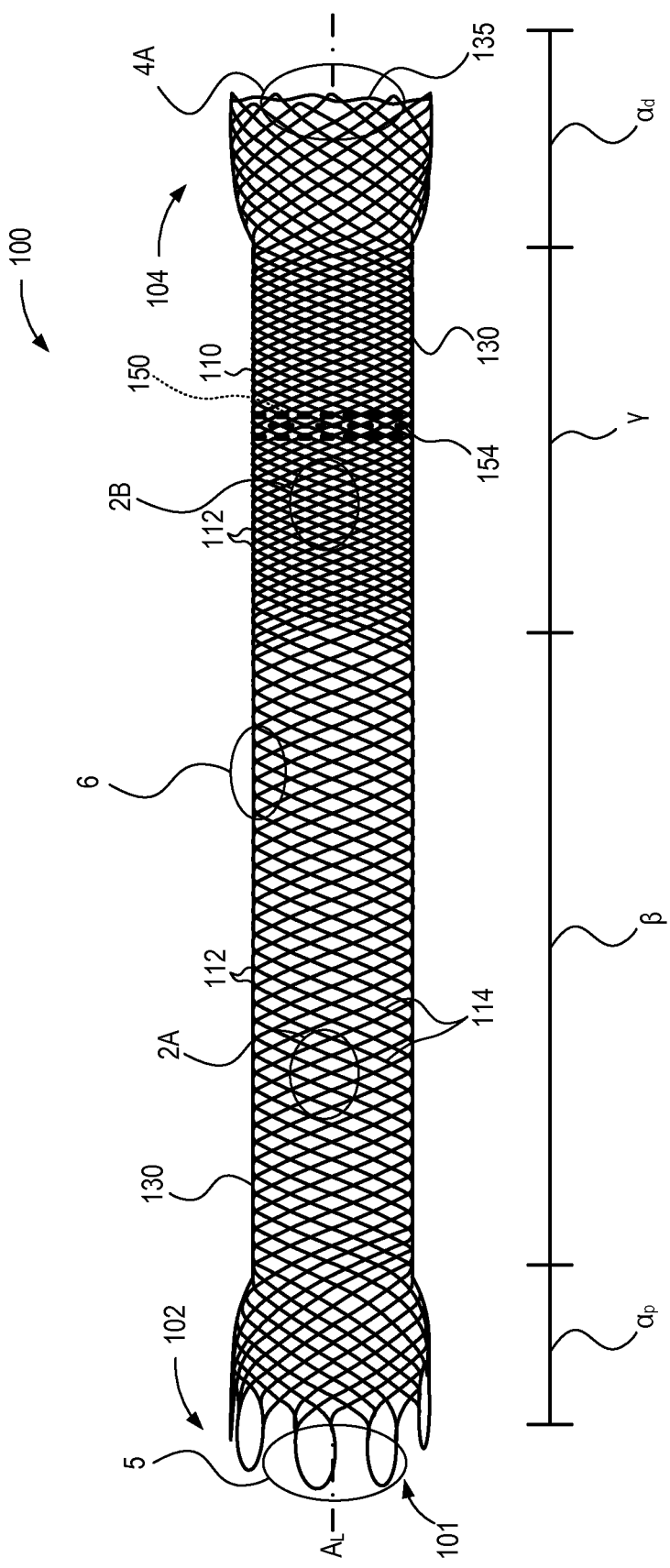
FIG. 1 is a side view of a stent, according to one embodiment.

Implantable medical devices are useful tools of modern medicine. In general, an implantable device is a device or structure configured to be inserted or embedded into a patient and serves one or more of a variety of functions. Implantable devices include, for example, stents, filters, markers, drug delivery devices, valves, and monitors.

A stent is an implantable device that is inserted into a body lumen, such as a vessel or a passage, to keep the lumen open and prevent closure due to a stricture, external compression, or internal obstruction. Stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer.

A stent may be configured with a support or scaffolding structure that may optionally be coupled to or coated with a cover. Additionally, the stent may comprise a variety of components, and the parameters of these components (e.g., shape, length, thickness, position, etc.) may be configured to provide a stent with certain properties. For example, the stent may be configured to distribute transverse loads or to change shape in response to certain forces. In some embodiments, the stent may also include a suture which may aid the user with repositioning or removal of the stent. Furthermore, the stent may comprise a valve which may be coupled to the inside diameter of the stent.

Though many of the examples provided herein refer to stents configured for use within the esophagus, the present disclosure is also applicable to a variety of stents designed for a variety of applications, such as biliary stents.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest to a practitioner during use, while the distal end is the opposite end. For example, the proximal end of a stent refers to the end nearest to the practitioner when the stent is disposed within, or being deployed from, a deployment device. For consistency throughout, these terms remain constant in the case of a deployed stent, regardless of the orientation of the stent within the body. In the case of an esophageal stent—deployed through the mouth of a patient—the proximal end will be nearer to the head of the patient and the distal end nearer to the stomach when the stent is in a deployed position.

FIG. 1 is a side view of a stent 100, according to one embodiment. As shown in the illustrated embodiment, the stent 100 may comprise a scaffolding structure 110 comprised of one or more braided or otherwise woven strand elements 112 (or strands 112). As used herein, a braid encompasses one or more strands 112 arranged (e.g., woven) in an interlaced pattern. The scaffolding structure 110 may define a generally cylindrical shape that has a proximal end 102, a distal end 104, and a lumen 101 formed through the generally cylindrical shape of the scaffolding structure 110. The lumen 101 may extend in the longitudinal direction (a direction along the longitudinal axis $A_L$) between the proximal end 102 and the distal end 104. The stent 100 may further include a cover 130 coupled to the scaffolding structure 110, a suture 135, and a valve 150.

The one or more strands 112 may be woven in a given pattern in accordance with an appropriate braid design, such as a closed-loop braid design, a single wire braid design, an endless braid design, or the like. The scaffolding structure 110 of the illustrated embodiment is configured as a closed-loop braid design in which multiple strands 112 are interlaced in a first direction (e.g., a distal direction) and then turn and are interlaced back in an opposite second direction (e.g., back in the proximal direction). The closed-loop braid design allows for fully automated or partially automated braiding (e.g., interlacing) of the multiple strands 112. In other embodiments, the scaffolding structure 110 may be configured as a single wire braid design in which a single strand 112 is braided (e.g., interlaced) with itself. Generally a scaffolding structure 110 having a single wire braid design is generated by hand, rather than an automated process. In still other embodiments, the scaffolding structure 110 may have an endless braid design in which multiple strands 112 are interlaced, generally by an automated process braiding in a single direction. An endless braid design may involve a braiding process that interlaces strands from one end to the other (e.g., does not involve a turn and return in the opposite direction).

The strands 112 forming the scaffolding structure 110 may comprise any suitable material known in the art, including plastics and memory alloys. In some embodiments, the scaffolding strands 112 may be Nitinol, including ASTM F2063. In one embodiment, the thickness of a memory alloy strand 112 of the scaffolding structure 110 may be between about 0.15 mm and about 0.30 mm, making the scaffolding structure 110 between 0.30 mm and 0.60 mm thick at points of intersection 114 of the braided strands 112 and between about 0.15 mm and about 0.30 mm at areas between the points of intersection 114 of the braided strands 112. In other embodiments, the thickness of the strands 112 of the scaffolding structure 110 may be between about 0.175 mm and about 0.275 mm. In other embodiments, the thickness of the strands 112 of the scaffolding structure 110 may be between about 0.20 mm and about 0.25 mm. In other embodiments, the thickness of the strands 112 of the scaffolding structure 110 may be about 0.225 mm.

The strands 112 of the illustrated embodiment of FIG. 1 are braided in a one-wire, one over-one under braid pattern, which is discussed more fully below with reference to FIGS. 2A and 2B. In other embodiments, the strands 112 can be braided in any of a variety of braid patterns. Other examples of braid patterns are shown in FIGS. 3A and 3B, and are described below with reference to the same.

The stent 100 of FIG. 1 further includes a cover 130 coupled to the scaffolding structure 110. The cover 130 can define an inner portion of the stent 100. The cover 130 may be elastomeric, polymeric, or comprised of any other material known in the art. In some embodiments, the cover may include silicone, while in certain embodiments the cover may be comprised only of silicone.

In some embodiments, the cover 130 may be applied such that it tends to ebb and flow into spaces between portions of the scaffolding structure 110 of a stent, resulting in a "tire tread" like outer surface, rather than a smooth outer cover. In some embodiments such a design may be configured to allow tissue to lock into the uneven spaces and treads, thus adding anti-migration properties in some instances.

In some embodiments the cover 130 may include multiple subparts or layers. For example, in some embodiments the cover 130 may be a two-part design. Such two-part covers may be composed of a base cover which encapsulates the scaffolding structure 110 and a second cover which may be applied after the first cover cures. In certain embodiments, the second cover may only be applied to the outside diameter of the stent 100 and may chemically bond to the first cover layer. For example, a stent may have a cover with a first layer comprised of a medical-grade silicone, such as TSP-8021, and a second layer applied to the outside diameter of a particularly low-friction silicone, such as Nusil MED-6670. In other embodiments, the second layer may comprise parylene. Multiple-layered covers may be configured such that the primary layer adds elasticity or resiliency to the stent while the second, outer layer reduces friction along the outside diameter. It is within the scope of this disclosure to use any of the exemplary materials for any of the layers.

In embodiments which utilize a particularly low-friction cover 130 on the outside diameter of the stent 100, the outer cover may be configured to more easily allow the stent to be loaded into a catheter and/or to decrease the catheter size needed to sheath the stent 100. Specifically, a low-friction outer layer, such as Nusil MED-6670 disclosed above, may reduce the coefficient of friction between a catheter and a stent by as much as 50% in some applications.

Further, an additional lubricant, such as Nusil MED-400, for example, may be utilized to increase the ergonomics of the system, allowing the stent 100 to be more easily loaded into, or deployed from, a catheter. In some embodiments, silicone lubricants may be used, including fluorinated polymers such as MED-400. Use of fluorination may reduce the solubility of the lubricant in some silicone elastomers; thus use of a fluorinated lubricant may reduce the tendency of the lubrication to dissolve into the silicone base over time.

In some embodiments, the cover 130 may be applied by bonding a polymer tube/sleeve to an inner diameter of the stent 100, leaving an outer diameter (surface) of the stent bare (e.g., uncovered or uncoated). Attaching the cover 130 to only the inner diameter of the stent 100 can improve flexibility, reduce a crimp profile to crimp the stent 100 into a catheter, reduce friction between a surface of stent when loading and/or deploying the stent 100, improve tire tread on the outer surface for migration properties, and allow elongation and foreshortening of the stent.

The stent 100 may further be configured with a valve 150. In some embodiments, such as the embodiment of FIG. 1, the valve 150 may be coupled to an inside diameter of the stent 100. Thus, the valve 150 is not directly visible in the illustration of FIG. 1, though its position is indicated by a reference line. A suture 154 may be used to secure the valve 150 to an inner diameter of the stent 100. For example, the suture 154 may secure the valve 150 to the one or more strands 112 of the scaffolding structure 110 of the stent 100. In another embodiment, the suture 154 may secure the valve 150 to a cover 130 of the stent 100. In another embodiment, a plurality of ties may be used to secure the valve 150 to an inner diameter of the stent 100.

In some embodiments, the stent 100 may include one or more zones or segments along the longitudinal length of the stent 100. More specifically, the scaffolding structure 110 may define a plurality of zones (or segments), which may have varying degrees of compressibility. In the illustrated embodiment of FIG. 1, the scaffolding structure 110 of the stent 100 includes four zones, namely a proximal end zone $\alpha_p$, a transition zone $\beta$, a valve zone $\gamma$, and a distal end zone $\alpha_d$. The stent 100 may be configured such that different zones of the stent 100 have different structural or geometric features or components. The stent 100 may also be configured such that different zones have different physical properties. For example, the end zones $\alpha_p$, $\alpha_d$ each flare and thus have a larger diameter than the transition zone $\beta$ and the valve zone $\gamma$. As another example, the stent 100 may be designed such that different zones have a different hoop force and crush force, which may result in varying degrees of compressibility.

As used herein, hoop force refers to the magnitude of a radial force applied around the circumference and toward a center longitudinal axis $A_L$ of the stent 100 that causes the stent 100 to collapse. Accordingly, a stent (or zone of a stent) with a relatively high hoop force may be more resistant to collapse when compared to a stent (or zone of a stent) with a relatively low hoop force. A stent designed with a low hoop force may therefore be easier to sheath and/or recapture.

As used herein, crush force refers to the magnitude of a two-dimensional force (e.g., pinch force) applied on the stent 100 in a transverse direction with respect to the center longitudinal axis $A_L$ that causes the stent 100 to deform. Accordingly, a stent (or zone of a stent) with a relatively high crush force may be more resistant to deformation by strictures or other physiological features when compared to a stent (or zone of a stent) with a relatively low crush force.

In some embodiments, the stent 100 may be configured with one or more zones that have a relatively low hoop force and a relatively high crush force. The one or more zones may allow the stent 100 to be easily sheathed or recaptured and may also be capable of resisting deformation by strictures or other physiological structures. In other embodiments, the stent 100 may be configured with one or more zones that have a hoop force and a crush force that are each relatively high or relatively low. In other embodiments, the stent 100 may be designed such that the hoop force and crush force vary between and/or within each zone of the stent 100.

In some embodiments, the stent 100 may be designed such that one or more zones may be relatively "soft" (e.g., more easily compressible, or less resistant to compression or deformation, in a transverse direction). As used herein, the term "soft" refers to areas with relatively low hoop force and relatively low crush force. In some applications, the relative softness of a particular zone, for example the proximal end zone $\alpha_p$, may be configured to cause less trauma to tissue that contacts the stent 100 when implanted. As another example, the end zones $\alpha_p$, $\alpha_d$ may be configured to be relatively "soft" as compared to the valve zone $\gamma$, particularly if the valve zone is a reinforced zone. Further, a stent 100 designed with a soft proximal end 102 (or a soft proximal end zone $\alpha_p$) may be more easily removed or repositioned.

Analogously, a stent 100 may be designed with one or more zones that are relatively "stiff" (e.g., less easily compressible, or more resistant to compression or deformation, in a transverse direction). As used herein, the term "stiff" refers to areas with relatively high hoop force and relatively high crush force. The relative stiffness of a particular zone may provide additional structure and support to prevent deformation and/or collapse of the stent 100. For example, the stiffness of a particular zone, for example the valve zone $\gamma$, may resist deformation by strictures or other physiological features or conditions at a therapy site. The stiffness of, for example, the valve zone $\gamma$ may also protect a valve 150 of the stent 100 from deformation and/or damage.

Softness or stiffness may be referred to as a degree of compressibility. A soft zone has a relatively high degree of compressibility (easily compressed or more compressible) as compared to a stiff zone that has a relatively low degree of compressibility (less easily compressed or less compressible). In some embodiments, the degree of compressibility of the various zones may vary. For example, the stent 100 may be configured with relatively soft zones and relatively stiff zones in order to tailor the stent 100 to a specific therapy. For example, designing the stent 100 with relatively soft (high degree of compressibility) end zones $\alpha_p$, $\alpha_d$ may result in relatively less discomfort, or pain, caused by contact of the stent ends with body tissue. Thus, in some embodiments the portion of the stent 100 configured to be implanted at the treatment location may be relatively stiff (low degree of compressibility), allowing it to resist stricture and otherwise function as part of a desired treatment, while other portions are relatively soft (high degree of compressibility) to reduce trauma and pain at those points. For example, in the illustrated embodiment of FIG. 1, the valve zone $\gamma$ may be configured to be more stiff (lower degree of compressibility) than other zones, such as the end zones $\alpha_p$, $\alpha_d$ and the transition zone $\beta$.

The degree of compressibility of a given zone (i.e., the relative softness or stiffness) may depend on various factors, including scaffolding design/construction, diameter of the strands, shape of the strands, braid pattern, braid angle, and presence and positioning of reinforcement members.

In some embodiments, a degree of compressibility of a given zone may differ from other zones because of a different braid angle of the braided strand element(s) 112 within the given zone as compared to other zones. A larger (higher) braid angle, approaching, for example, 90 degrees, results in a higher pick count (number of points of intersection 114 of the strands 112) per given longitudinal length (e.g., an inch) of a given braid pattern. The higher pick count can produce greater stiffness (i.e., a lower degree of compressibility). A smaller (lower) braid angle results in a lower pick count per given longitudinal length, which can result in greater softness (i.e., a higher degree of compressibility). Accordingly, a different braid angle in different zones can configure the scaffolding structure to have different zones of differing degrees of compressibility.

In the embodiment of FIG. 1, the valve zone $\gamma$ has a higher braid angle than the braid angle of the transition zone $\beta$ and, thus, a greater number of points of intersection 114 of the strands 112 than the transition zone $\beta$, which can result in greater stiffness or a lower degree of compressibility than the transition zone $\beta$. A comparison of FIGS. 2A and 2B illustrates a differing braid angle and its effect on the scaffolding structure 110.

Figure 2A:
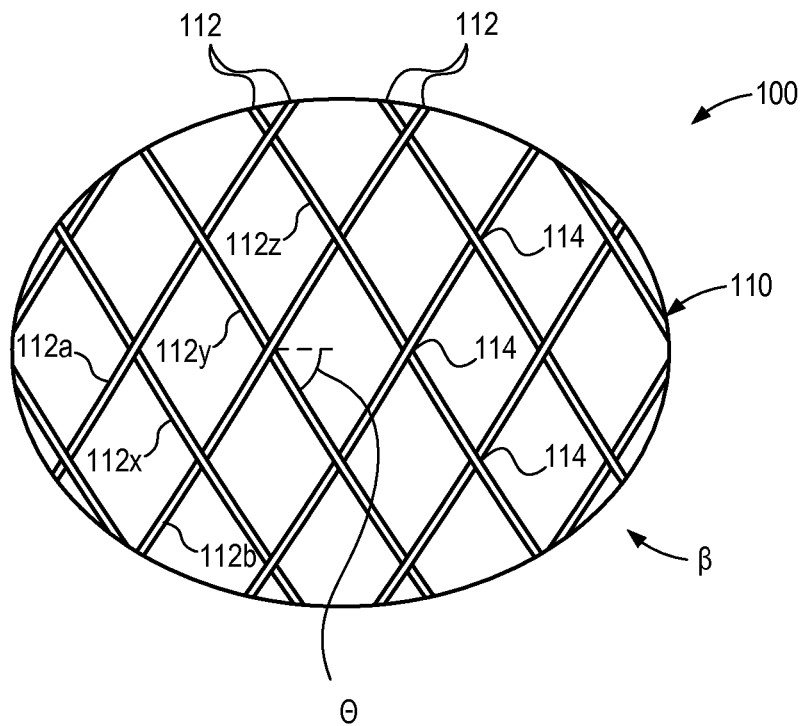
FIG. 2A is a close-up view of a portion of the stent of FIG. 1.
Figure 3A:
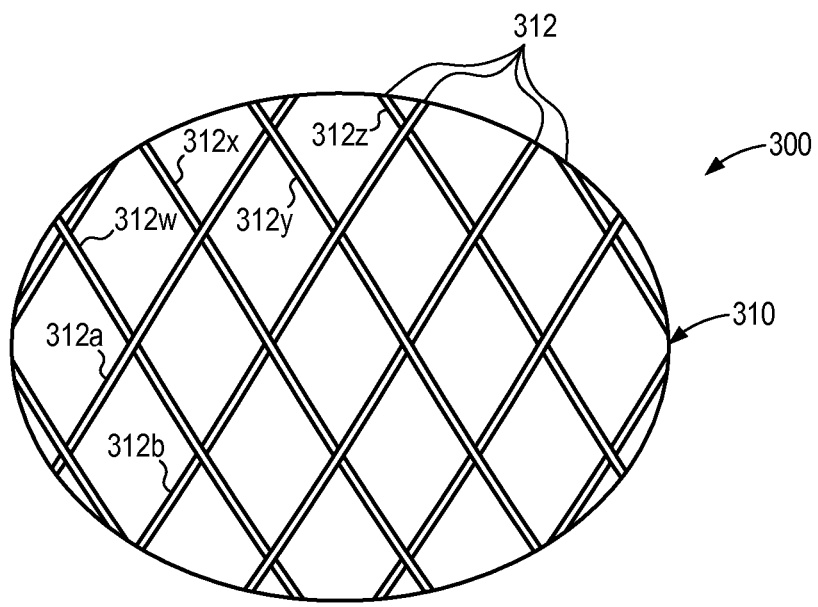
FIG. 3A is a close-up view of a portion of a stent, according to another embodiment, illustrating a braid pattern.
Figure 3B:
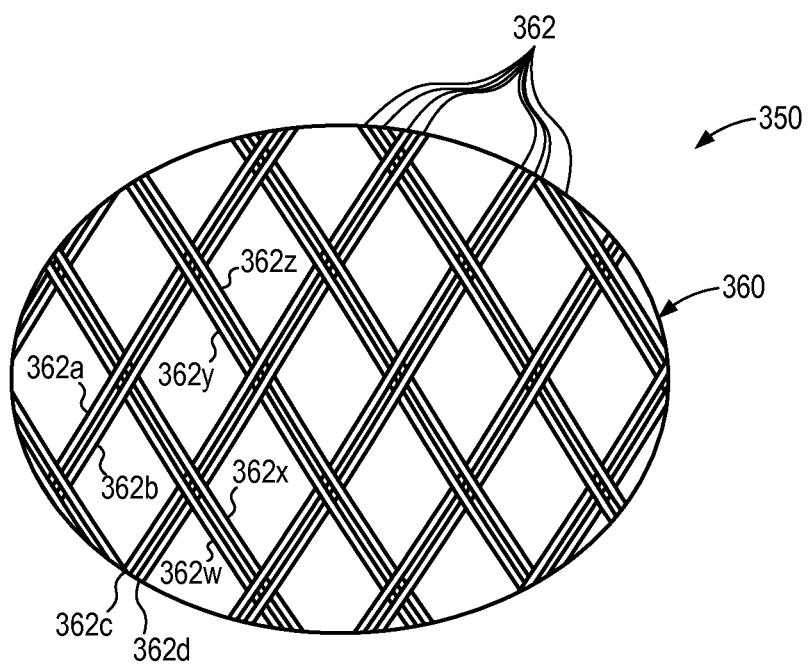
FIG. 3B is a close-up view of a portion of a stent, according to another embodiment, illustrating a braid pattern.

FIG. 2A is a close-up view of a portion of the transition zone $\beta$ of the scaffolding structure 110 of the stent 100 of FIG. 1. This close-up view illustrates the braid pattern and the braid angle $\theta$ of the transition zone $\beta$. The braid pattern of the transition zone $\beta$ (and of the entire scaffolding structure 110) is a one-wire, one over-one under braid pattern, which means that a single strand 112 passes over another strand 112 (or another portion of itself, such as in a single wire braid design) and then under another strand 112 (or yet another portion of itself, such as in a single wire braid design). Specifically, a first strand 112a (or a first length 112a of a single strand 112) passes over a first intersecting strand 112x (or a first intersecting length 112x of a single strand 112) and then passes under a second intersecting strand 112y (or a second intersecting length 112y of a single strand 112). The first strand 112a (or a first length 112a) may then repeat the pattern passing over the top of a third intersecting strand 112z (or third intersecting length 112z), etc. An adjacent second strand 112b (or a second length 112b of a single strand) alternates the pattern, first passing under the first intersecting strand 112x (or the first intersecting length 112x) and then passing over the top of the second intersecting strand 112y (or the second intersecting length 112y).

The braid angle θ is an angle formed by a given strand 112, such as the first strand 112a, and the longitudinal axis $A_L$ of the stent, as illustrated in FIG. 2A. A larger (higher) braid angle, approaching, for example, 90 degrees, results in a higher pick count (number of points of intersection 114 of the strands 112) per given longitudinal length (e.g., an inch) of a given braid pattern. The higher pick count can produce greater stiffness (i.e., a lower degree of compressibility). A smaller (lower) braid angle results in a lower pick count per given longitudinal length, which can result in greater softness (i.e., less stiffness and a higher degree of compressibility). Accordingly, a different braid angle in different zones can configure the scaffolding structure to have different zones of differing degrees of compressibility. In the illustrated embodiment of FIGS. 1, 2A, and 2B, the braid angle θ within the transition zone β of the scaffolding structure 110 is relatively moderate and the braid angle within the valve zone γ may be relatively high, compared to other zones, such as the transition zone β. The relatively high braid angle θ within the valve zone γ may give the scaffolding structure greater hoop strength and/or crush strength, and correspondingly a lower degree of compressibility.

Figure 2B:
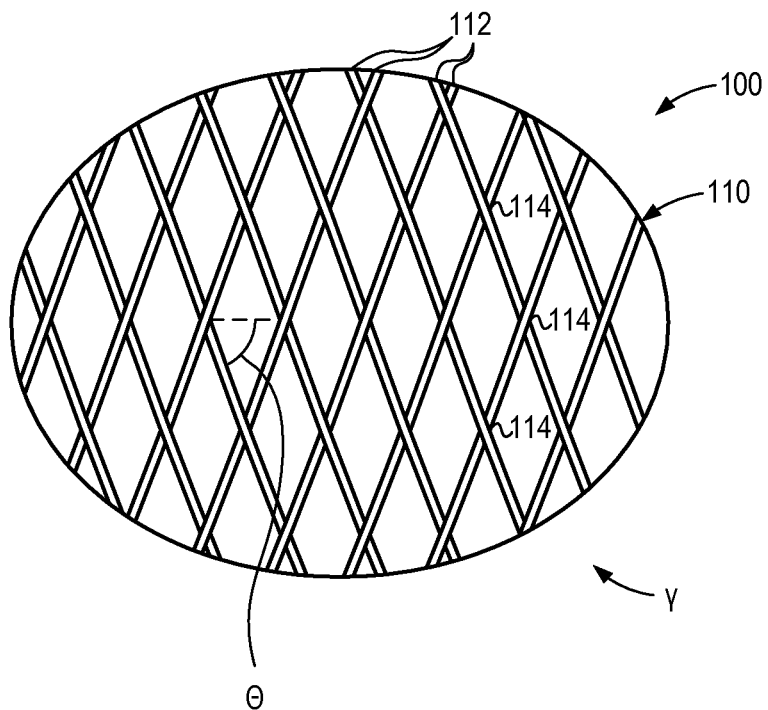
FIG. 2B is a close-up view of a portion of the stent of FIG. 1.

FIG. 2B is a close up view of a portion of the valve zone γ of the scaffolding structure 110 of the stent 100 of FIG. 1. This close up view illustrates the braid pattern and the braid angle θ of the valve zone γ. The braid pattern of the transition zone β is the same pattern as the valve zone γ, namely a one-wire, one over-one under braid pattern. Although the braid pattern of both the transition zone β and the valve zone γ is the same, the braid angle θ of each of the zones β, γ is different. The braid angle θ of the valve zone γ is larger (higher) than the braid angle of the transition zone β, which may result in the valve zone γ being stiffer and having a lower degree of compressibility than the transition zone β.

FIG. 3A is a close-up view of a portion of a stent 300, according to one embodiment, illustrating a braid pattern. In the illustrated embodiment, a scaffolding structure 310 of the stent 300 has one or more strands 312 arranged in a braid pattern. The braid pattern is a one-wire, two over-two under braid pattern, which means that a single strand 312 passes over two other strands 312 (or two other portions of itself, such as in a single wire braid design) and then under two more strands 312 (or yet two other portions of itself, such as in a single wire braid design). Specifically, a first strand 312a (or a first length 312a of a single strand 312) passes over a first intersecting strand 312w and a second intersecting strand 312x (or over two intersecting lengths 312w, 312x of a single strand 312) and then passes under a third intersecting strand 312y and a fourth intersecting strand 312z (or under two more intersecting lengths 312y, 312z of a single strand 312). The pattern then repeats. An adjacent second strand 312b (or a second length 312b of a single strand 312) passes under the first and second intersecting strands 312w, 312x and then passes over the third and fourth intersecting strands 312y, 312z.

FIG. 3B is a close-up view of a portion of a stent 350, according to one embodiment, illustrating another braid pattern. In the illustrated embodiment, a scaffolding structure 360 of the stent 350 has one or more strands 362 arranged in yet another braid pattern. The braid pattern is a two-wire, one over-one under braid pattern, which means that a pair of strands 362 (or a pair of lengths of a strand, such as in a single wire braid design) pass over another strand 362 (or another portion of itself, such as in a single wire braid design) and then under another strand 362 (or yet another portion of itself, such as in a single wire braid design). Specifically, a first strand 362a and a second strand 362b (or first and second lengths 362a, 362b of a single strand 362) together pass over a first intersecting strand 362w (or a first intersecting length 362w of a single strand 362) and a second intersecting strand 362x (or a second intersecting length 362x of a single strand 362). The first strand 362a and the second strand 362b then together pass under a third intersecting strand 362y (or a third intersecting length 362y) and a fourth intersecting strand 362z (or a fourth intersecting length 362z of a single strand 362). The first strand 362a and the second strand 362b are adjacent to one another and may be parallel within portions of the pattern (or even through the length of the scaffolding structure 360). Similarly, the first and second intersecting strands 362w, 362x and/or the third and fourth intersecting strands 362y, 362z may be parallel within portions of the pattern (or through the length of the scaffolding structure 360). The first strand 362a and the second strand 362b may then repeat the pattern passing over the top of a third intersecting strand 362z (or a third intersecting length 362z), etc. An adjacent pair of strands 362c, 362d (or an adjacent pair of lengths 362c, 362d of a single strand) alternates the pattern, first passing under the first intersecting strand 362x and then passing over the second intersecting strand 362y.

A skilled artisan can appreciate that a stent or implantable device of the present disclosure may have a construction of any of a single wire braid design, and endless braid design, or a closed-loop design and that such construction may utilize any suitable braid pattern, including but not limited to: the one-wire, one over-one under braid pattern illustrated in FIGS. 1, 2A, and 2B; the one-wire, two over-two under braid pattern illustrated in FIG. 3A; and the two-wire, one over-one under braid pattern illustrated in FIG. 3B. The braid angle of any of the braid patterns can be altered (increased/decreased) as desired to define zones of varying degrees of compressibility as desired for a given treatment or stent application.

Figure 4:
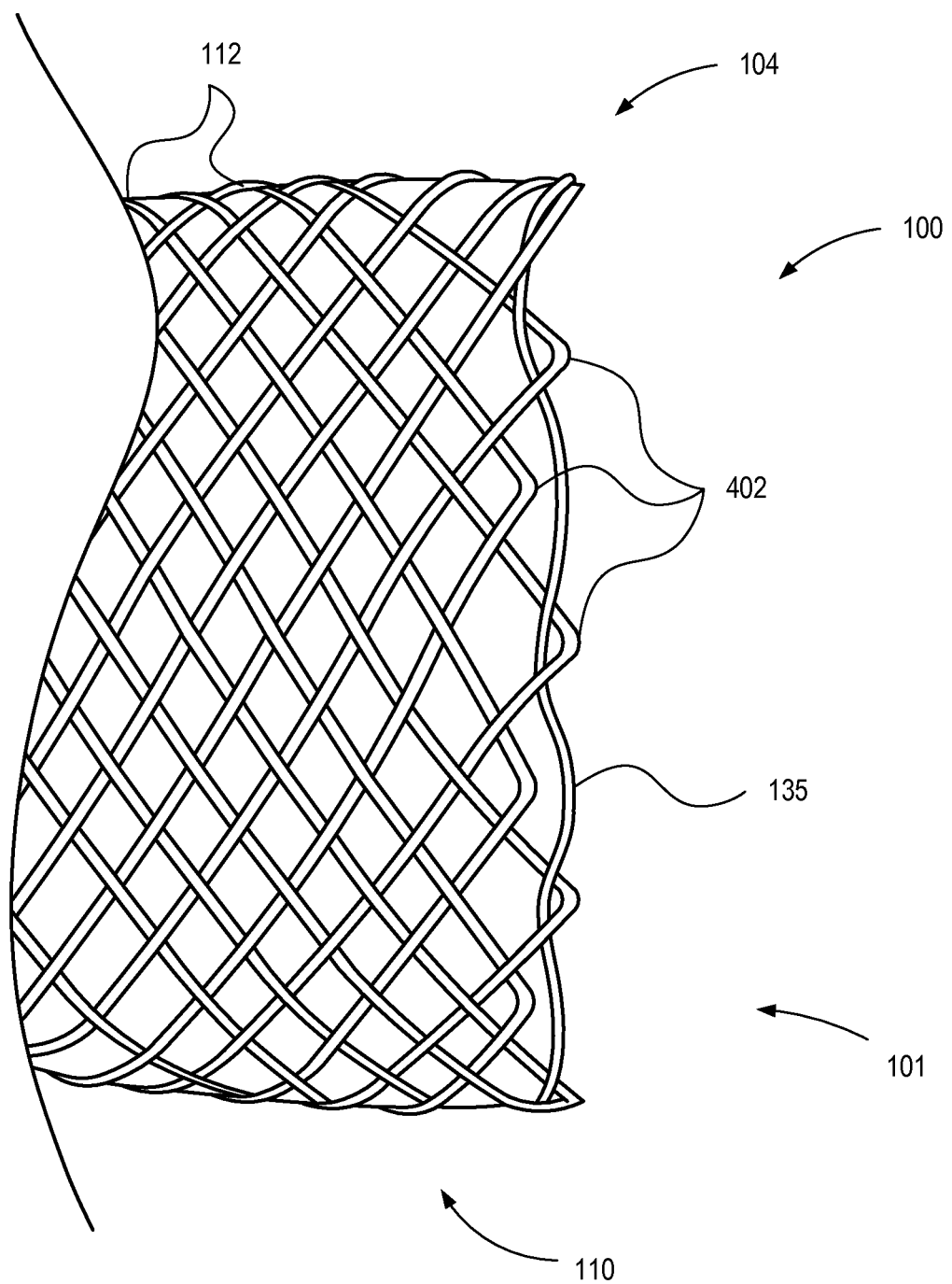
FIG. 4 is a close-up view of a distal end of the stent of FIG. 1.

FIG. 4 is a close-up view of a distal end 104 of the stent 100 of FIG. 1. The close-up view illustrates the strands 112 of the scaffolding structure 110 turning back in the closed-loop braid design to form loops 402. As described above, in a closed-loop design each strand 112 of the braiding pattern proceeds from a first end (e.g., the proximal end) in a in a given direction (e.g., a distal direction), and at the opposite end (e.g., the distal end) of the stent the strands bend or turn back to form a loop 402 and return in the direction they came from (e.g., in the proximal direction) toward the first end. The shape and design of the loops 402 may distribute the expansive force of a stent 100 acting on a body lumen when the stent 100 is deployed. For example, a rounded shape of the loops 402 may be configured to lessen trauma to body tissue that contacts the distal end 104 of the stent 100.

A suture 135 can be positioned through all or a portion of the loops 402 to aid a user in repositioning or removal of the stent 100. The loops 402 may function to secure the suture 135 to the scaffolding structure 110 of the stent 100. Pulling the suture 135, for example in the distal direction, may cause a purse-string effect to cause the stent 100, or at least a distal end 104 of the stent 100, to at least partially collapse. A tool may be manipulated through the lumen 101 of the stent to engage the suture 135 and pull or otherwise force a portion of the suture 135 in the distal direction to effect a purse string collapse of the distal end 104 of the stent 100.

Figure 5A:
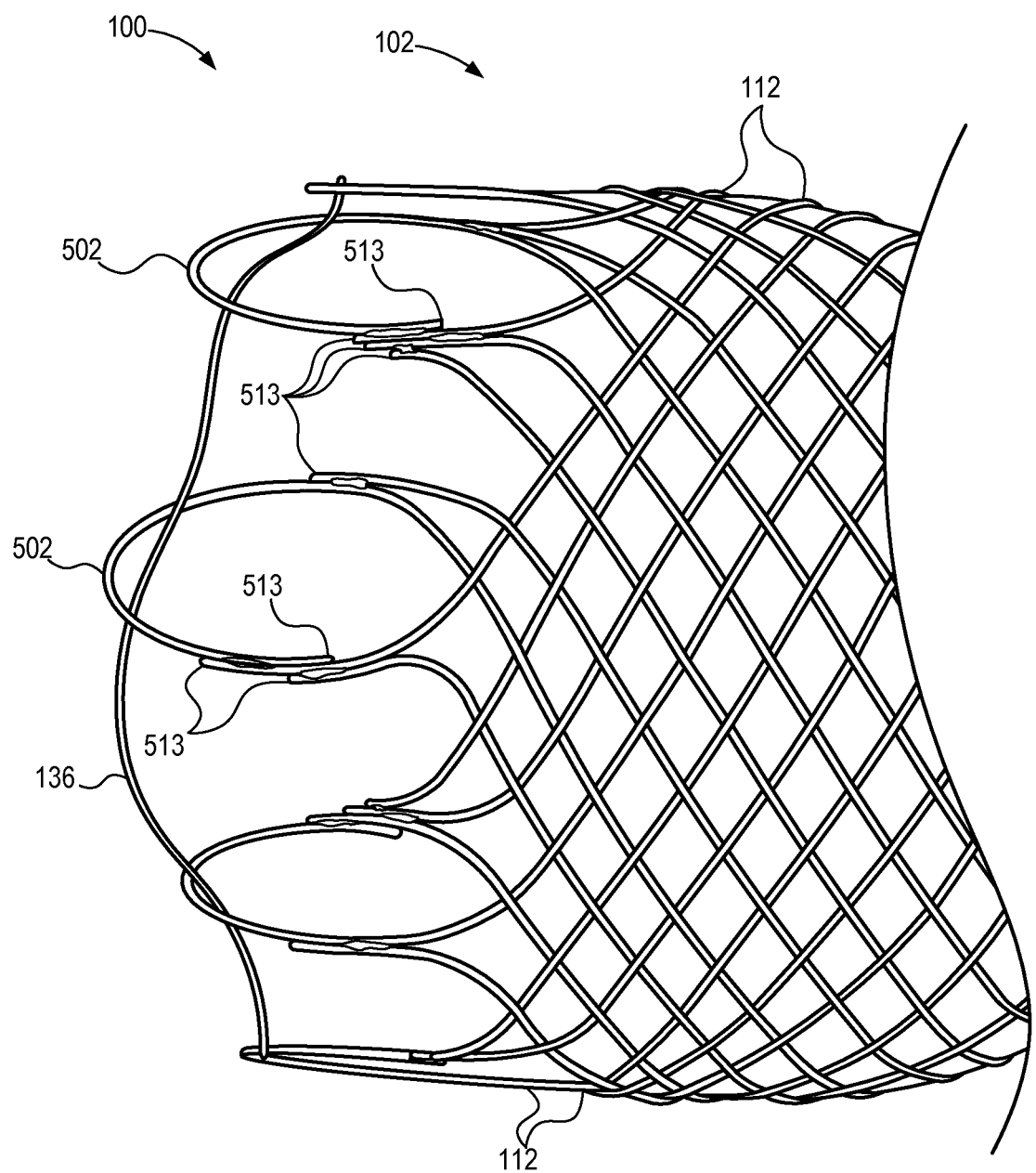
FIG. 5A is a close-up view of a proximal end of the stent of FIG. 1.

FIG. 5A is a close-up view of a proximal end 102 of the stent 100 of FIG. 1. The close-up view of FIG. 5A illustrates loops 502 formed by connecting together free ends 513 of one or more strands 112. As previously described, in a closed-loop braid design the one or more strands 112 of the scaffolding structure 110 may proceed from the proximal end 102 to the distal end 104 in the braid pattern and then turn and return back to the proximal end 102. Accordingly, the two free ends of a strand 112 are disposed at the proximal end 102 of the stent 100. The free ends can be configured and coupled together to form a loop 502. The close-up view of FIG. 5A illustrates the free ends of the strands 112 of the scaffolding structure 110 joined together to form the loops 502.

The shape and design of the loops 502 may distribute the expansive force of the stent 100 acting on a body lumen when the stent 100 is deployed. For example, a rounded shape of the loops 502 may be configured to lessen trauma to body tissue that contacts the proximal end 102 of the stent 100.

The free ends of a strand 112 may be joined in any number of ways to form a loop 502, including but not limited to crimping, welding, gluing, coating, twisting, tying, and any other appropriate coupling mechanism.

A suture 536 can be positioned through all or a portion of the loops 502 to aid a user in repositioning or removal of the stent 100, similar to the suture 135 described above with respect to FIG. 4. The loops 502 may function to secure the suture to the scaffolding structure 110 of the stent 100. Pulling the suture, for example in the proximal direction, may cause a purse-string effect to cause the stent 100, or at least a proximal end 104 of the stent 100, to at least partially collapse. The collapsed proximal end 104 may then be repositioned or drawn into a catheter for removal from the body lumen.

Figure 5B:
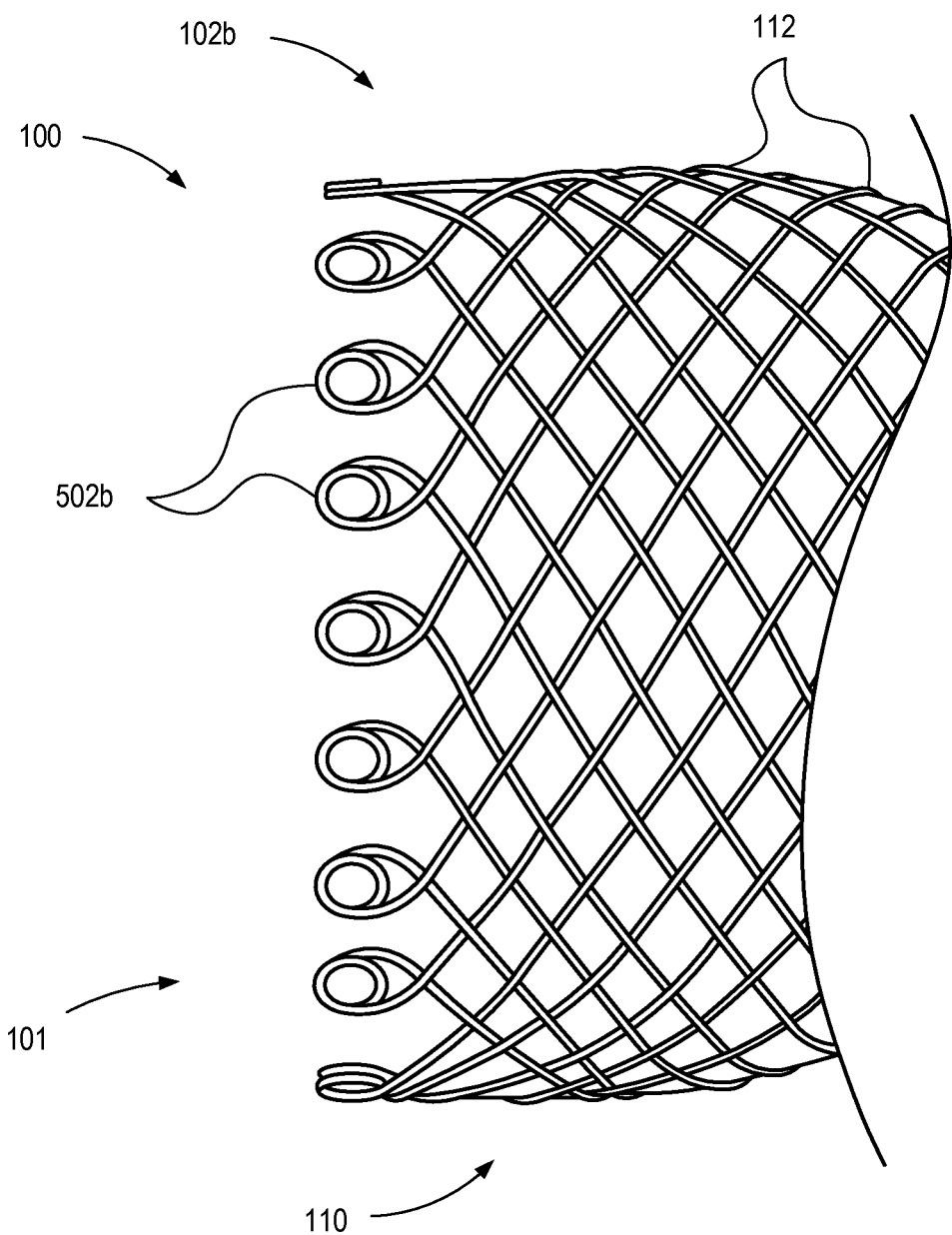
FIG. 5B is a close-up view of a proximal end of a stent, according to another embodiment.

FIG. 5B is a close-up view of an alternative proximal end 102b of the stent 100, according to another embodiment, illustrating fully closed loops 502b that may be disposed at the proximal end 102b. The scaffolding structure 110 of the stent 100 is a closed-loop design, similar to the design of the embodiment of FIG. 5A. The close-up view of FIG. 5B illustrates the free ends of the strands 112 of the scaffolding structure 110 coupled together and/or turned through a full turn (e.g., greater than 360 degrees). The full turn of the strands 112 forms the loops 502b and provides the loops 502b a closed configuration.

A suture (not shown) can be positioned through the loops 502b to aid a user in repositioning or removal of the stent 100, similar to the suture 136 described above with respect to FIG. 5A. The fully closed configuration of the loops 502b can function to ensure that a suture remains properly and appropriately positioned within the loops 502b and at the end of the stent 100.

Figure 6:
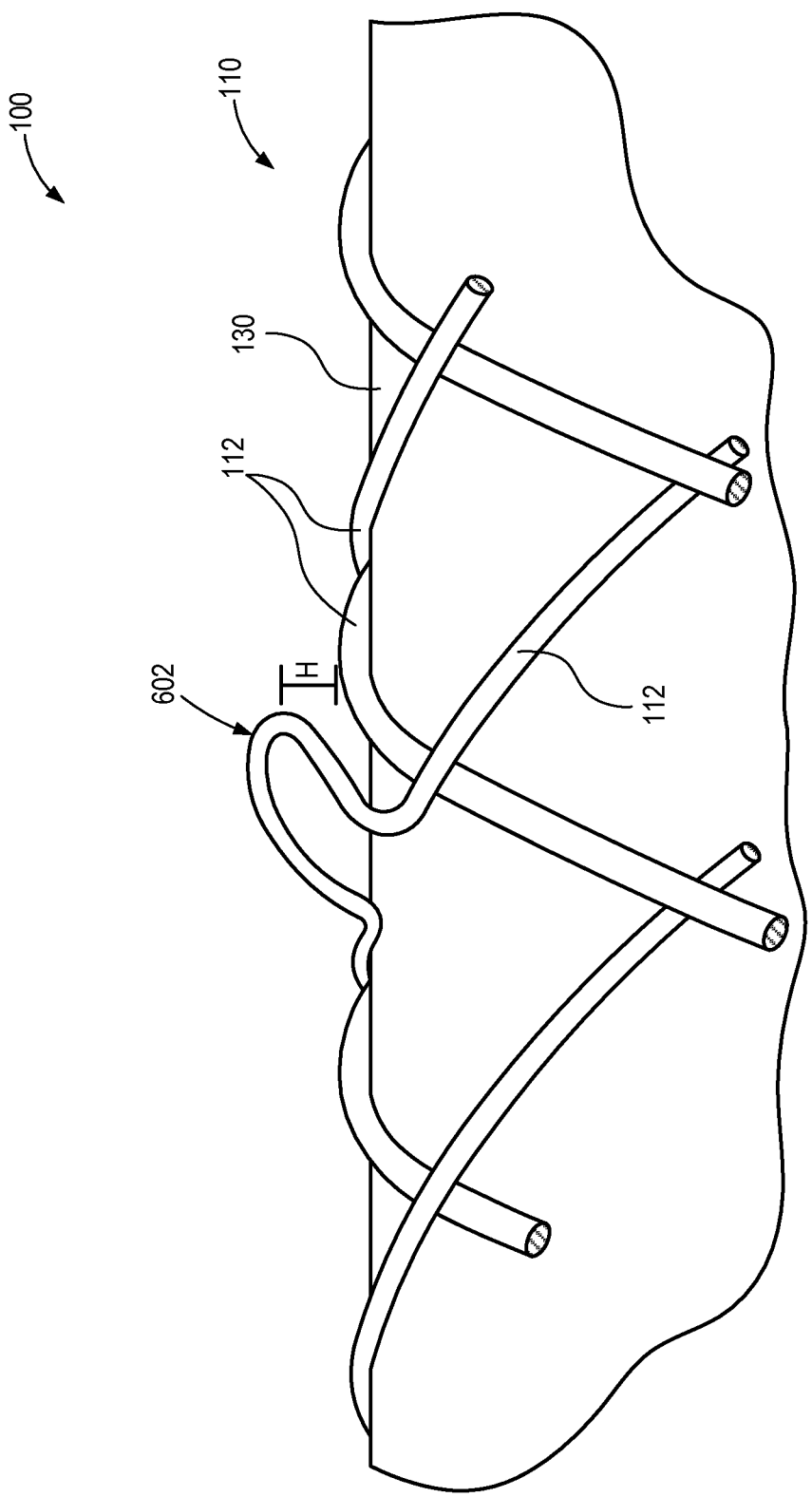
FIG. 6 is a side close up view of a portion of the stent of FIG. 1.

FIG. 6 is a side close-up view of a portion of the stent 100 of FIG. 1. As depicted in FIG. 6, in certain embodiments, the scaffolding structure 110 may include one or more anti-migration features 602 to aid in securing the stent 100 in a fixed position within the body lumen that is subject to treatment with the stent 100. The anti-migration features 602 may include a bend in a strand 112 of the scaffolding structure 110. A bend forming the anti-migration feature 602 may be oriented to protrude outward, away from an outer surface (or outer diameter) of the stent 100. For example, the anti-migration feature 602 may be configured such that the distance H that the end of the anti-migration feature 602 is displaced outwardly from the outside diameter of the stent 100 may be between about 0.1 mm and about 0.9 mm. In some embodiments, the distance H may be between about 0.3 mm and about 0.7 mm. In some embodiments, the distance H may be about 0.5 mm. This arrangement may allow the anti-migration feature 602 to engage the body lumen and minimize migration of the stent 100. In some embodiments, each anti-migration feature 602 may be disposed outwardly, though in other embodiments not every anti-migration portion may be so disposed.

In other embodiments, the anti-migration features 602 may comprise a full turn (e.g., 360-degrees or more), similar in design to the loops 502b illustrated in FIG. 5B and described above with reference to the same.

The total number of anti-migration features 602 may vary depending on the size of the stent 100 and the application for which it is configured. For example, an esophageal stent having a length of about 100 mm may include from about 10 to about 25 anti-migration features 602, including about 20 total anti-migration features 602. Similarly, an esophageal stent having a length of about 120 mm may include from about 15 to 35 anti-migration features 602, including about 30 total anti-migration features 602, and an esophageal stent having a length of about 150 mm may include from about 20 to 45 anti-migration features 602, including about 40 anti-migration features 602.

In the embodiment of FIG. 6, the anti-migration feature 602 is disposed in a distally oriented direction, thus configured to minimize migration of the stent 100 in the distal direction. In the case of an esophageal stent, such a design may be configured to counteract the peristaltic forces of the esophagus. In other embodiments, some or all of the anti-migration features 602 may likewise be disposed in the proximally oriented direction to minimize migration of the stent 100 in the proximal direction.

The scaffolding structure 110 of FIG. 6 is illustrated as being positioned outside of the cover 130. A skilled artisan can appreciate that in other embodiments, the cover 130 may coat outer surfaces of the scaffolding structure 110, including coating the anti-migration features 602. The cover 130 may be disposed on an outer surface of the scaffolding structure 110. In still other embodiments, the cover 130 may be disposed on an inner surface and an outer surface (and/or may coat all surfaces) of the strands 112.

Figure 7:
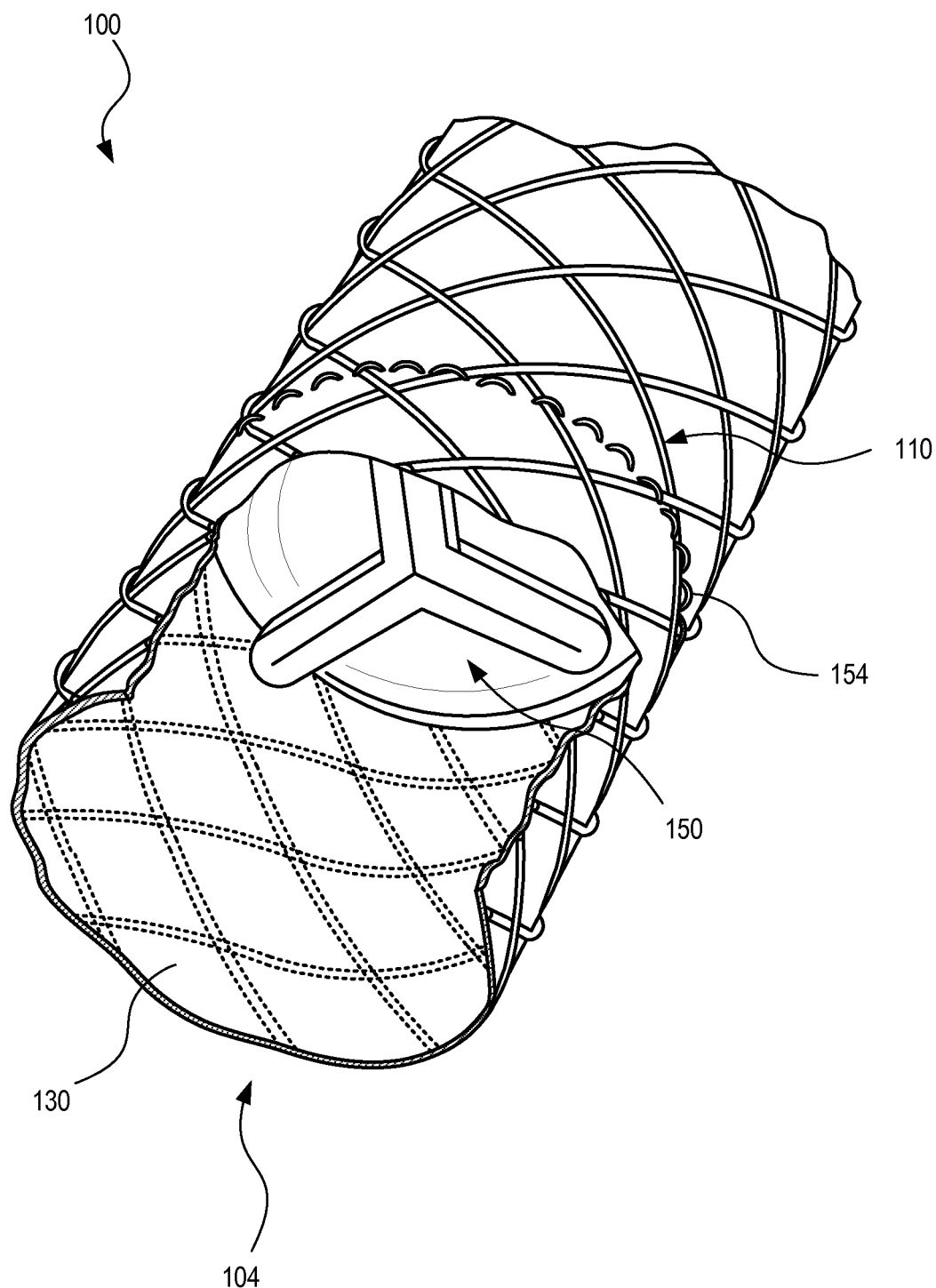
FIG. 7 is a cut-away perspective view of the stent of FIG. 1.

FIG. 7 is a cut-away perspective view of a distal portion of the stent 100 of FIG. 1, including the valve 150. A cut-away of the distal end 104 of the stent 100 is shown, including a cover 130, and a scaffolding structure 110. The stent 100 is oriented such that the valve 150 is visible through the cut-away portion and/or opening at the distal end 104 of the stent 100. In other embodiments, the valve 150 may be positioned at other locations along the longitudinal length of the stent 100, including locations closer to the proximal end 102 (not shown in FIG. 7, but see FIG. 1) or distal end 104 of the stent 100. For example, the valve 150 may be positioned at the distal end 104 such that a portion of the valve may hang outside of the scaffolding structure 110 of the stent 100. Accordingly, the valve 150 may be positioned at any point and in any portion of the stent 100.

Figure 8A:
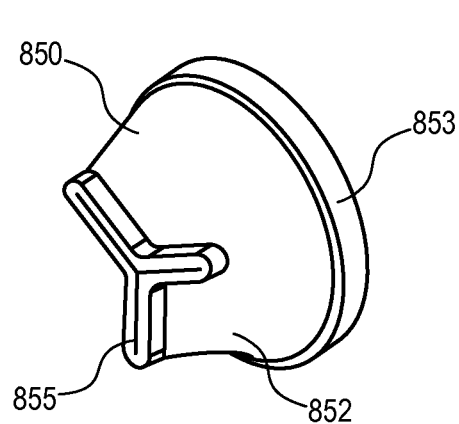
FIG. 8A is a perspective view of a valve for use with a stent, according to one embodiment.
Figure 8B:
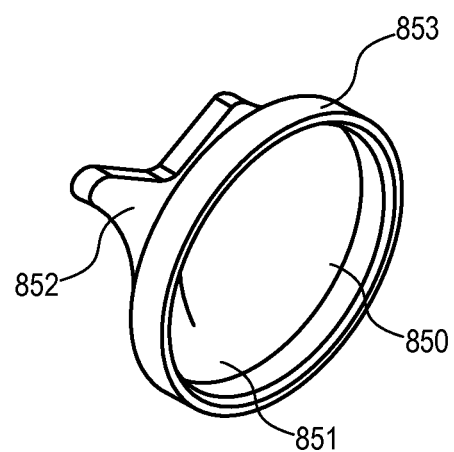
FIG. 8B is a second perspective view of the valve of FIG. 8A.
Figure 8C:
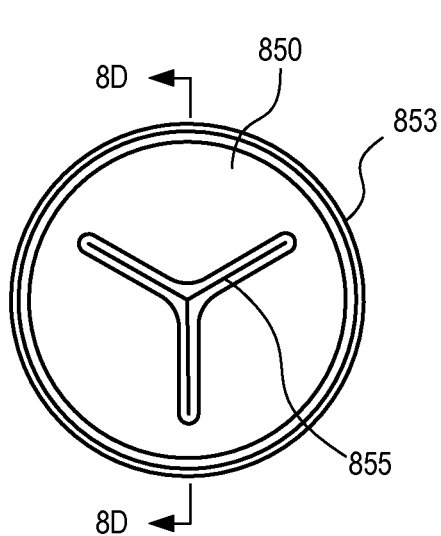
FIG. 8C is a top view of the valve of FIG. 8A.

FIGS. 8A-8D are multiple views of a valve 850 configured for use with a stent, according to one embodiment. Specifically, FIG. 8A is a perspective view of the valve 850, FIG. 8B is a second perspective view of the valve 850, FIG.

Figure 8D:
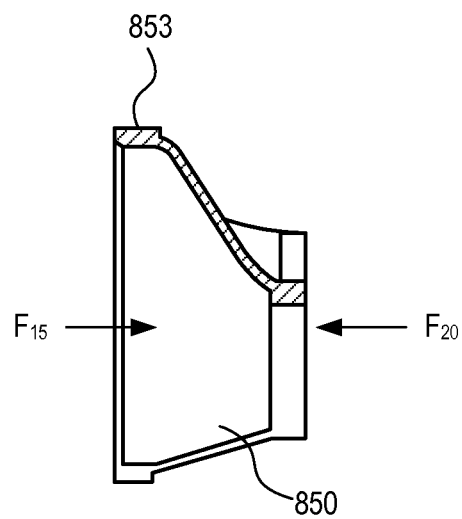
FIG. 8D is a cross-sectional view of the valve of FIG. 8C, taken through line 8D-8D.

8C is a top view of the valve 850, and FIG. 8D is a cross-sectional view of the valve taken through line 8D-8D.

Referring generally and collectively to FIGS. 8A-8D, the valve 850 may be formed of an elastomeric or a polymeric material and may comprise an upper surface 851, a lower surface 852, and a rim 853. The rim 853 may provide structure and support to the valve 850 as well as provide a location at which the valve 850 may be coupled to a stent, for example, by stitching.

The valve 850 may further comprise an opening 855 which is closed when the valve 850 is not actuated. In the illustrated embodiment, the valve opening 855 comprises three intersecting slits in the valve body. The valve opening 855 may be opened in response to a force acting on the upper surface 851 of the valve 850. Likewise, the valve may be opened by a force acting on the lower surface 852 of the valve 850. The shape and design of the valve 850 may be such that the force required to open the valve 850 by acting on the lower surface 852 is much larger than the force required to open the valve 850 by acting on the upper surface 851. For example, FIG. 8D illustrates two forces: $F_{15}$ acting on the upper surface 851 of the valve 850 and $F_{20}$ acting on the lower surface 852 of the valve 850. In response to $F_{15}$, the three-sided valve opening 855 may open relatively easily, as opposing sides of the opening 855 are pushed away from each other. Contrarily, in order for $F_{20}$ to open the valve 850, the entire lower surface 852 must deform, folding in on itself until the valve opening 855 is located on the opposite side of the rim 853. Thus, the valve 850 may be designed such that it is more easily opened from one direction than the other.

In the case of esophageal stents, a valve such as valve 850 may be positioned such that the lower surface 852 faces the stomach while the upper surface 851 faces the mouth. In this orientation, the valve 850 may more readily open to allow food to pass to the stomach, but generally will prevent reflux from the stomach, except in response to a relatively large force—for instance when a patient belches or vomits.

Notwithstanding the specific disclosure provided in connection with FIGS. 8A-8D, it is within the scope of the current disclosure to utilize a stent with any type or design of valve, or without a valve at all.

Figure 9:
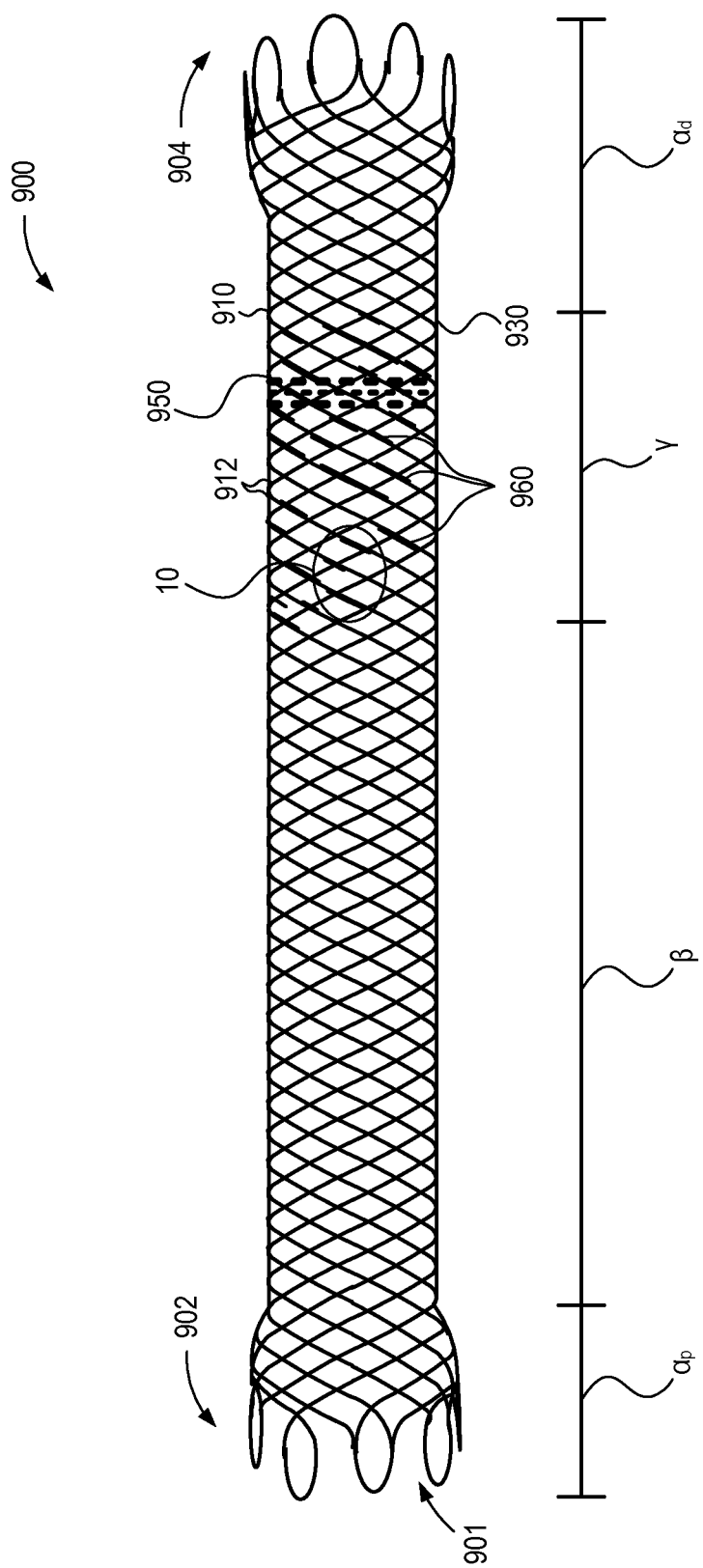
FIG. 9 is a side view of a stent, according to one embodiment.

FIG. 9 is a side view of a stent 900, according to one embodiment. As shown in the illustrated embodiment, the stent 900 may comprise a scaffolding structure 910 comprised of one or more braided or otherwise woven strand elements 912 (or strands 912). As used herein, a braid encompasses one or more strands 912 arranged (e.g., woven) in an interlaced pattern. The scaffolding structure 910 may define a generally cylindrical shape that has a proximal end 902, a distal end 904, and a lumen 901 formed through the generally cylindrical shape of the scaffolding structure 910. The lumen 901 may extend in the longitudinal direction (a direction along the longitudinal axis $A_L$) between the proximal end 902 and the distal end 904. The stent 900 may further include a cover 930 coupled to the scaffolding structure 910 and a valve 950.

The scaffolding structure 910 of the illustrated embodiment may include one or more functional members 960, which may be added to achieve certain desired functional characteristics. For example, the functional members 960 may include, but are not limited to, reinforcement members, drug eluting members, radiopaque members and/or fluoroscopic markers, kink resistance members, and torque optimization members. The functional members 960 may be zero-angle elements or filaments that may be coupled to or otherwise attached to one or more strands 912 of the scaffolding structure 910, for example, by crimping, weaving, gluing, welding, tying, and the like to provide an added functional characteristic or to otherwise enhance the scaffolding structure 910.

In the embodiment of FIG. 9, the functional members 960 are reinforcement member 960. A reinforcement member 960 may be a zero-angle element that may be coupled to a strand 912 of the scaffolding structure 910 at a given position to reinforce and/or increase stiffness of the stent in proximity to the given position. The reinforcement members 960 may be formed of Kevlar or similar durable material to provide a stiffening effect at a given area. The positioning of the reinforcement members 960 define and/or reinforce one or more zones or segments along the longitudinal length of the stent 900. In the illustrated embodiment of FIG. 9, the scaffolding structure 910 of the stent 900 includes four zones, namely a proximal end zone $\alpha_p$; a transition zone $\beta$; a valve zone $\gamma$, and a distal end zone $\alpha_d$.

The stent 900 may be configured such that different zones of the stent 100 have different structural or geometric features or components. The stent 100 may also be configured such that different zones have different physical properties. For example, the end zones $\alpha_p$, $\alpha_d$ each flare and thus have a larger diameter than the transition zone $\beta$ and the valve zone $\gamma$. As another example, the stent 100 may be designed such that different zones have a different hoop force and crush force, which may result in varying degrees of compressibility. In the illustrated embodiment of FIG. 9, the degree of compressibility of a given zone, such as the valve zone $\gamma$, may be decreased (i.e., the zone may be made more stiff) by the reinforcement members 960. The reinforcement members 960 may support, stabilize, or otherwise reinforce a given length of a strand 912, thereby increasing hoop strength or crush strength at the area of the reinforcement member 960.

Figure 10:
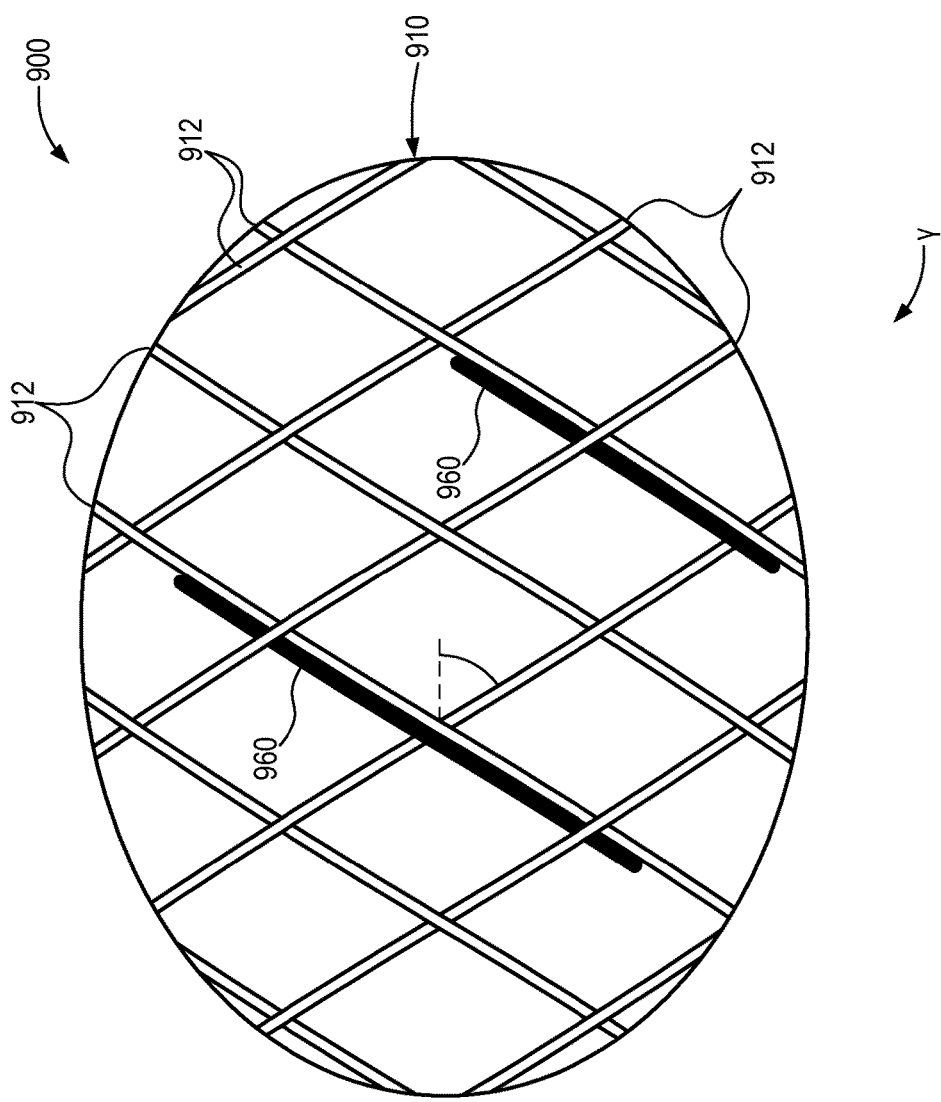
FIG. 10 is a close-up view of a portion of the stent of FIG. 9.

FIG. 10 is a close-up view of a portion of the stent 900 of FIG. 9. The close-up view illustrates the valve zone $\gamma$ of the scaffolding structure 910. The scaffolding structure 910 in the valve zone $\gamma$ includes reinforcement members 960 coupled to one or more strands 912 to reinforce the valve zone $\gamma$ and decrease the degree of compressibility of the valve zone $\gamma$.

In other embodiments, a degree of compressibility of a given zone of a valve, such as the valve zone $\gamma$, may be decreased by a combination of an increased braid angle $\theta$, as described above with reference to FIGS. 1, 2A, and 2B, and by including reinforcement members 960.

In other embodiments, the functional member 960 may be a radiopaque marker, such as a small extruded tube (formed of platinum or other radiopaque material) that can be slid over a strand 916 and fixed in position by the interlacing ("criss-cross") pattern.

Other examples of embodiments of the present disclosure include the following:

Example 1

A method of manufacturing an implantable device to be disposed within a body lumen, comprising: braiding one or more strand elements in a braid pattern to form a scaffolding structure configured to provide support to the body lumen, the scaffolding defining a generally cylindrical shape and a lumen through the scaffolding structure, wherein the scaffolding structure comprises one or more strand elements braided in a braid pattern; and coupling a valve to an inside diameter of the scaffolding structure.

Example 2

The method of Example 1, further comprising: forming a plurality of zones in the scaffolding structure, wherein a degree of compressibility of a first zone of the plurality of zones differs from a degree of compressibility of a second zone of the plurality of zones based on a braid angle of the one or more strand elements within the first zone being different from a braid angle within the second zone.

Example 3

The method of Example 2, further comprising: forming an anti-migration feature in a middle zone of the plurality of zones of the scaffolding structure by forming a 180-degree bend in a strand element oriented to protrude outwardly from an outer surface of the scaffolding structure.

Example 4

The method of Example 3, further comprising: integrating a reinforcement member into the scaffolding structure to define a reinforced zone of the plurality of zones, the reinforced zone having a lower degree of compressibility than another zone of the plurality of zones.

The examples and embodiments disclosed herein are to be construed as merely illustrative and exemplary, and not a limitation of the scope of the present disclosure in any way.

It will be obvious to those having skill in the art that many changes may be made to the details of the above-described embodiments without departing from the underlying principles of the invention. The scope of the present invention should, therefore, be determined only by the following claims.

The invention claimed is:

1. An implantable device to be disposed within a body lumen, the implantable device comprising:
   a scaffolding structure comprising one or more strand elements arranged in an interlaced braid pattern, the scaffolding structure comprising a plurality of zones disposed along a longitudinal length of the scaffolding structure, the scaffolding structure being configured to provide support to the body lumen, the scaffolding defining a cylindrical shape and a lumen through the scaffolding structure, the scaffolding structure comprising:
      a first portion of the interlaced braid pattern comprising a first zone of the plurality of zones having a first uniform diameter and a first compressibility;
      a second portion of the interlaced braid pattern comprising a second zone of the plurality of zones having a second uniform diameter that is the same as the first uniform diameter and a second compressibility that is less than the first compressibility due to features of the scaffolding structure;
      a third portion of the interlaced braid pattern comprising a third zone of the plurality of zones having a third uniform diameter greater than the first uniform diameter and a third compressibility that is greater than the first compressibility due to features of the scaffolding structure; and
      a fourth portion of the interlaced braid pattern comprising a fourth zone of the plurality of zones having a fourth uniform diameter substantially equivalent to the third uniform diameter and a fourth compressibility substantially equivalent to the third compressibility due to features of the scaffolding structure;
   a valve coupled to an inside diameter of the scaffolding structure; and
   a polymeric cover that is attached to the scaffolding structure such that the cover extends across the entire longitudinal length of the scaffolding structure and between adjacent strand segments of the interlaced braid pattern of the scaffolding structure;
   wherein each strand element of the one or more strand elements extends substantially along the entire longitudinal length of the scaffold structure.

2. The implantable device of claim 1, wherein a degree of compressibility of a given zone of the plurality of zones differs from another zone of the plurality of zones based on a different braid angle of the one or more strand elements within the given zone, wherein the given zone having a given braid angle is more compressible than another zone having a smaller braid angle.

3. The implantable device of claim 1, further comprising a functional member secured to a strand in a given zone of the plurality of zones of the scaffolding structure.

4. The implantable device of claim 3, wherein the functional member is a reinforcement member, wherein a degree of compressibility of the given zone is further decreased due to the reinforcement member.

5. The implantable device of claim 1, wherein the plurality of zones includes a valve zone, wherein the valve zone is less compressible in a transverse direction than any other zone of the plurality of zones due to features of the scaffolding structure, and the valve is coupled to the valve zone of the scaffolding structure.

6. The implantable device of claim 1, further comprising a plurality of eyelets configured to receive a suture, the plurality of eyelets formed by the one or more braided strand elements, the plurality of eyelets disposed at a first longitudinal end of the cylindrical shape.

7. The implantable device of claim 1, wherein the polymeric cover comprises a first layer and a second layer, and wherein at least one of the first and second layers comprises silicone.

8. The implantable device of claim 1, further comprising one or more radiopaque indicia indicating a position of the valve.

9. The implantable device of claim 1, wherein the scaffolding structure comprises an anti-migration feature formed in a zone of the plurality of zones of the scaffolding structure, the anti-migration feature comprising a bend in a strand element oriented to protrude outwardly from an outer surface of the scaffolding structure.

10. The implantable device of claim 1, wherein the scaffolding structure comprises a plurality of anti-migration features formed in a middle zone of the plurality of zones of the scaffolding structure, each anti-migration feature of the plurality of anti-migration features formed by a bend in a strand element of the one or more strand elements of the scaffolding structure, each anti-migration feature oriented to protrude outwardly from an outer surface of the scaffolding structure.

11. An implantable device to be disposed within a body lumen, the implantable device comprising:
   a scaffolding structure defining a cylindrical shape and a lumen through the scaffolding structure, wherein the scaffolding structure comprises one or more strand elements arranged in an interlaced braid pattern defining a first zone and a second zone, the first zone forming a first portion of a lumen having a first uniform diameter and the second zone forming a second portion of the lumen having a second uniform diameter, wherein the first uniform diameter and the second uniform diameter are the same, the second zone comprising a higher pick count than the first zone, wherein the scaffolding structure further comprises a third zone disposed at a first longitudinal end of the scaffolding structure, wherein the second zone is disposed between the first zone and the third zone, and wherein a compressibility of the third zone is greater than a compressibility of the first zone; and a valve coupled to an inside diameter of the second zone of the scaffolding structure; and an anti-migration feature formed in a middle zone of the scaffolding structure by a 180-degree bend in a strand element of the scaffolding structure oriented to protrude outwardly and distally from an outer surface of the scaffolding structure to engage with a wall of the body lumen and prevent migration of the scaffolding structure relative to the wall of the body lumen.

12. The implantable device of claim 11, wherein a degree of compressibility of the first zone differs from a degree of compressibility of the second zone based on a braid angle of the one or more braided strand elements within the first zone being lower than a braid angle within the second zone.

13. The implantable device of claim 11, further comprising a functional member coupled to a portion of the second zone.

14. The implantable device of claim 13, wherein the functional member is a reinforcing member and a degree of compressibility of the second zone is decreased due to the reinforcement member.

15. The implantable device of claim 11, wherein the second zone comprises a valve zone, wherein the valve zone is less compressible in a transverse direction than other zones of the scaffolding structure due to features of the scaffolding structure, and wherein the valve is coupled to the scaffolding structure within the valve zone.

16. The implantable device of claim 11, wherein the scaffolding structure comprises a single-strand element braided in a single-wire braid design.

17. The implantable device of claim 11, wherein the scaffolding structure comprises multiple strand elements.

18. The implantable device of claim 11, wherein the scaffolding structure comprises an anti-migration feature formed in a middle zone of the scaffolding structure by a 180-degree bend in a strand element oriented to protrude outwardly from an outer surface of the scaffolding structure.

19. The implantable device of claim 11, further comprising a polymeric cover that is attached to the scaffolding structure such that the cover extends across the entire longitudinal length of the scaffolding structure and between adjacent strand segments of the interlaced braid pattern of the scaffolding structure.

20. The implantable device of claim 11, wherein the scaffolding structure further comprises a fourth zone disposed at a second longitudinal end of the scaffolding structure, and wherein a compressibility of the fourth zone is greater than a compressibility of the first zone.

21. An implantable device to be disposed within a body lumen, the implantable device comprising:

a scaffolding structure defining a cylindrical shape and a lumen through the scaffolding structure, the scaffolding structure comprising one or more strand elements arranged in an interlaced braid pattern, the scaffolding structure configured in a plurality of zones;

one or more reinforcement members integrated into the scaffolding structure to define a first reinforced zone of the plurality of zones, the first reinforced zone having a lower degree of compressibility than another zone of the plurality of zones comprising a common uniform diameter with the first reinforced zone, wherein the lower degree of compressibility of the first reinforced zone is due to at least one of the braid pattern, braid angle, and presence or positioning of the one or more reinforcement members; and a valve coupled to an inside diameter of the first reinforced zone of the scaffolding structure;

wherein each reinforcement member of the one or more reinforcement members runs lengthwise along a portion of a strand element of the one or more strand elements that is arranged in the interlaced braid pattern such that each reinforcement member is in contact with the strand element along the entire length of the reinforcement member, wherein the one or more reinforcement members are only disposed in the first reinforced zone, and wherein each reinforcement member weaves over or under adjacent strand segments;

wherein a braid angle of the first reinforced zone is greater than a braid angle of another zone of the plurality of zones; and wherein a pick count of the first reinforced zone is greater than a pick count of the second zone.

22. The implantable device of claim 21, wherein at least one reinforcement member of the one or more reinforcement members comprises a radiopaque indicium to indicate a position of the valve.

23. The implantable device of claim 21, wherein the scaffolding structure comprises one or more anti-migration features formed in the scaffolding structure, each anti-migration feature of the one or more anti-migration features formed by a bend in a strand element of the scaffolding structure oriented to protrude outwardly away from an outer surface of the scaffolding structure.

* * * * *